(12) United States Patent
de Haan

(10) Patent No.: US 6,275,030 B1
(45) Date of Patent: Aug. 14, 2001

(54) APPARATUS FOR DETERMINING PROPERTIES OF AN ELECTRICALLY CONDUCTIVE OBJECT

(75) Inventor: V. O. de Haan, Puttershoek (NL)

(73) Assignee: Röntgen Technische Dienst B.V., Rotterdam (NL)

( * ) Notice: Subject to any disclaimer, the term of this patent is extended or adjusted under 35 U.S.C. 154(b) by 0 days.

(21) Appl. No.: 09/355,867
(22) PCT Filed: Feb. 2, 1998
(86) PCT No.: PCT/NL98/00065
  § 371 Date: Nov. 9, 1999
  § 102(e) Date: Nov. 9, 1999
(87) PCT Pub. No.: WO98/34104
  PCT Pub. Date: Aug. 6, 1998

(30) Foreign Application Priority Data

Jan. 31, 1997 (NL) .................................................. 1005160

(51) Int. Cl.[7] .................................................. G01R 33/12
(52) U.S. Cl. ........................... 324/229; 324/239; 702/170
(58) Field of Search .................................. 324/229, 240, 324/202, 239, 230, 231, 207.16; 702/97, 170, 64; 165/11.2

(56) References Cited

U.S. PATENT DOCUMENTS

| | | | |
|---|---|---|---|
| 3,597,678 | * | 8/1971 | Fearon .................................... 324/37 |
| 5,339,256 | * | 8/1994 | Levy et al. ............................ 364/506 |
| 5,525,903 | * | 6/1996 | Mandl et al. ......................... 324/230 |
| 5,680,042 | * | 10/1997 | Griffen et al. ................... 324/207.21 |

\* cited by examiner

*Primary Examiner*—Christine Oda
*Assistant Examiner*—Anthony Jolly
(74) *Attorney, Agent, or Firm*—Varnum, Riddering, Schmidt & Howlett LLP

(57) ABSTRACT

Eddy currents are generated in an object constructed of a conductive material by transmitting an electromagnetic signal to the object and detecting electromagnetic signals generated by eddy currents induced in the object, and an electromagnetic signal V(t) is described by a product of two factors F and G(t), wherein F is a function of the geometry and electrical and magnetic properties of the material and G(t) is a function of geometry of the material, the electrical and magnetic properties of the material, the thickness perpendicular to the surface of the material, and time.

14 Claims, 1 Drawing Sheet

APPARATUS FOR DETERMINING PROPERTIES OF AN ELECTRICALLY CONDUCTIVE OBJECT

BACKGROUND OF THE INVENTION

1. Field of the Invention

This invention relates to a method for describing an electromagnetic signal generated by eddy currents in a conductive material.

Such a method can be used inter alia in determining properties of an electrically conductive measuring object composed of that material. This invention relates in particular to a method for determining properties of an electrically conductive measuring object, wherein:

a. utilizing at least one transmitting antenna, an electromagnetic field changing over time is emitted to the measuring object for generating eddy currents in the object;

b. utilizing at least one receiving antenna, the electromagnetic signal generated by the eddy currents is detected; and c. on the basis of the detected electromagnetic signal, the properties of the measuring object are determined.

This invention further relates to an apparatus for practising such a method.

2. Description of Related Art

Such a method and apparatus are known from, for instance, U.S. Pat. No. 4,843,319. In this known method and apparatus, by means of a transmitting coil, a pulsated electromagnetic field is generated in the material of the measuring object. This gives rise to time-dependent eddy currents in the material. These eddy currents are detected by means of a receiving coil. The eddy currents, which change with time, cause a changing magnetic flux through the receiving coil, so that an induction voltage prevails across the receiving coil. Utilizing an amplifier, this changing induction voltage can be registered as a function of time. Thus, the electromagnetic signal generated by the eddy currents is detected as a function of the time t.

With the known apparatus, it is stated that the time-dependent behavior of the signal for small times t is determined by a constant logarithmic rate of decay of about 1.5. In other words, the received signal can be described with a signal V(t), to which the following relation applies: $d(\ln V)/d(\ln t) = -1.5$.

Beyond a certain critical time, designated $\tau$ and which is directly proportional to the square of the thickness of the surface of the material of the object under examination, so that $\tau = cd^2$, the logarithmic rate of decay falls to a lower value which equals $A - 2.17 \ln(t)$. In other words, the following applies where t is greater than $\tau$: $d(\ln V)/d(\ln t) = A - 2.17 \ln(t)$. Here A is determined by the material properties and the geometry of the measuring object. Accordingly, before the thickness of the measuring object can be determined, first the constants c and A are to be determined. Determining the constants c and A is carried out through two measurements on two different test objects of the same material but having different, homogeneous wall thicknesses. This means that for carrying out the method, at all times two mutually different test specimens are to be at hand. Further, in this known method and apparatus, from a single measurement, only the homogeneous wall thickness of the material can be computed. Furthermore, the apparatus is limited to the use of a receiving coil for measuring the signal.

SUMMARY OF THE INVENTION

The invention contemplates a solution to the disadvantages outlined above. Accordingly, an object of the invention is to provide a method and apparatus wherein for detecting the wall thickness of a measuring object, only a single measurement on a test object is to be performed beforehand. Another object of the invention is to make it possible to determine the distribution of wall thicknesses of the material of the measuring object. A further object of the invention is to determine, instead of the wall thicknesses, the permeability and the conductivity of the material of the measuring object. It is even possible to determine the spread in the conductivity or the spread in the relative permeability of the material. In order to provide a basis for carrying out such methods, the method for describing an electromagnetic signal generated by eddy currents in an electrically conductive material is characterized, according to the invention, in that the signal V(t) is described by at least one product of two factors F and G(t), where F is a function of the geometry of the material and the electrical and magnetic properties of the material, and where G(t) is a function of the geometry of the material, the electrical and magnetic properties of the material, the thickness perpendicular to the surface of the material and time.

The method according to the invention, in which said description of the signal is utilized for determining properties of an electrically conductive measuring object, is characterized in that utilizing a predetermined algorithm, parameters $$\frac{\sigma_i}{\mu_i}$$

or parameters to be derived from these parameters of the equation $$V(t) = \sum_{i=1}^{n} \theta_i F_i G_i(t) \qquad (1)$$

or equation to be derived therefrom, with $$F_i = \delta \sqrt{\frac{\sigma_i}{\mu_i}} \qquad (2)$$

$$G_i(t) = \frac{t^\gamma}{1 + \alpha\left(\beta \frac{t}{\tau_i}\right)^m e^{\beta \frac{t}{\tau_i}}} \qquad (3)$$

$$i = 1, 2, \ldots n \qquad (4)$$

and $$\sum_{i=1}^{n} \theta_i = 1 \qquad (5)$$

are selected such that V(t) according to a predetermined criterion of the algorithm corresponds to the course over time of the detected electromagnetic signal, where $\alpha$, $\beta$, $\gamma$, $\delta$ and m are real numbers which are dependent on the geometry of the measuring object, the transmitting antenna and the receiving antenna, as well as on the relative positions of the object, the transmitting antenna and the receiving antenna, $\mu_i$ represents the magnetic permeability of an area i of the measuring object and $\sigma_i$ represents the electrical conductivity of the area i of the measuring object, and the areas i (i=1, 2, . . . , n) together generate the detected electromagnetic signal.

When with this method the thickness $d_i$ of the material is to be determined, it is necessary only once, using a test object, to determine the magnetic permeability and the electrical conductivity of the material. The values of α, β, γ, δ and m can, in principle, given a known geometry of the transmitting antenna, receiving antenna and the object, be priorly calculated on the basis of a simulation model. When the conductivity or relative permeability is known, it is possible, using the method outlined above, to determine the wall thickness of the material on the basis of the formula $\tau_i = \mu_i \sigma_i d_i^2$ with i=n=1. It is also possible to determine the distribution of wall thicknesses of the material, given a known conductivity and a known relative permeability of the material, with n≧2.

The invention further makes it possible to determine the conductivity and the relative permeability of the material, given a known wall thickness. It is even possible to determine the spread in the conductivity or the spread in the relative permeability of the material, given a known wall thickness.

BRIEF DESCRIPTION OF THE DRAWINGS

The above will be further explained with reference to the drawing, in which.

DETAILED DESCRIPTION

Figure 1:
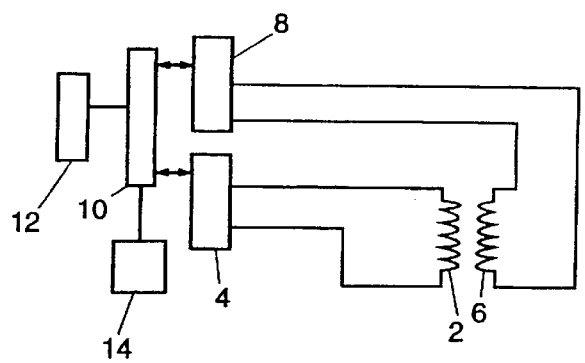
FIG. 1 shows a possible embodiment of an apparatus according to the invention for practising a method according to the invention on a measuring object.
Figure 1:
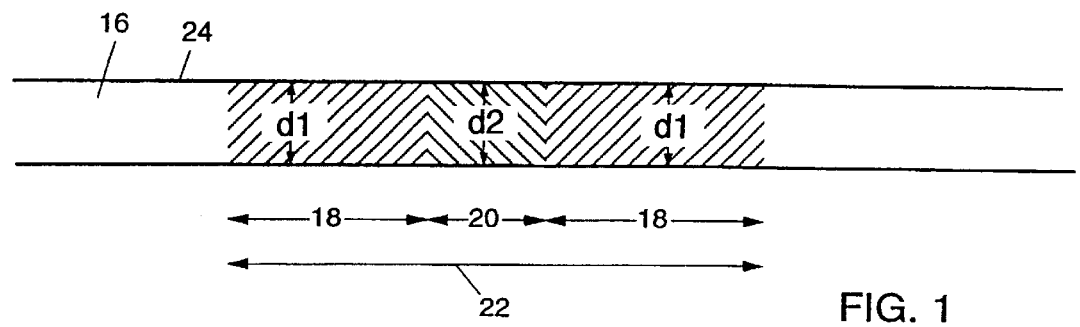

The apparatus 1 according to FIG. 1 comprises a transmitting antenna 2 in the form of a coil which is coupled to a transmitter unit 4. Further, the apparatus comprises a receiving antenna 6, similarly in the form of a receiving coil, which is coupled to a receiver unit 8. The transmitter unit 4 and the receiver unit 8 are coupled to a computer 10.

The apparatus further comprises an input unit 12, in this example a keyboard, and a display 14, each connected to the computer 10.

FIG. 1 further shows a measuring object 16. Properties of the measuring object, such as its thickness, magnetic permeability and electrical conductivity, can be measured by means of the apparatus 1. If the thickness, the magnetic permeability and the electrical conductivity are the same throughout, the entire measuring area, which is designated in FIG. 1 by the arrow 22, can be considered homogeneous. It is also possible, however, that within the measuring area 22 different thicknesses occur, for instance a thickness $d_{i=1}$ in the area i=1, which is indicated in FIG. 1 by the arrows 18, and a thickness $d_{i=2}$ in the area i=2, which is indicated in FIG. 1 by the arrow 20. Also,, the thickness may be the same throughout, while in the area i=1 the magnetic permeability $\mu_{i=1}$ and/or the electrical conductivity $\sigma_{i=1}$ differs from the magnetic permeability $\mu_{i=2}$ and/or the electrical conductivity $\sigma_{1=2}$ in the area i=2.

The operation of the apparatus is as follows. Using the transmitter unit 4 and the transmitting coil 2, a pulsating electromagnetic field is generated in the measuring area 22 of the object 16. In this example, the assumption is that a pulse to the generated electromagnetic field can be described with the ideal dirac pulse. However, this is not necessary to the invention.

The electromagnetic field thus generated in the measuring area 22 and varying, will have as a result that eddy currents are generated. According to Lenz's law, the flow of those eddy currents is such that the change of the electromagnetic field is counteracted. These eddy currents, in turn, generate a changing electromagnetic field, so that according to Faraday's law an induction voltage arises on the receiving coil 6. In other words, the receiving coil 6 detects an electromagnetic signal that is generated by the eddy currents. This electromagnetic signal is measured by means of the receiver unit 8 and applied to the computer 10. The measured electromagnetic signal is here described with S(t). In all particular embodiments of the method according to the invention to be described in more detail hereinafter, the assumption is that the measured signal S(t) can be described by a signal V(t) which comprises at least one product of two factors F and G(t), where F is a function of the geometry of the measuring object 16 and the electrical and magnetic properties of the material of the measuring object 16. G(t) is also a function of the geometry of the measuring object 16, the electrical and magnetic properties of the material of the measuring object 16, the thickness perpendicular to the surface 24 of the measuring object 16 and time.

Because the changing electromagnetic field is emitted using the transmitting antenna 2 and because the electromagnetic signal is detected using the receiving antenna 6, factors F and G are each also a function of the geometry of the transmitting and receiving antennas, as well as of the relative positions of the transmitting antenna, the receiving antenna and the measuring object.

More particularly, according to the invention, the following approximation for the signal V(t) has been found:

$$V(t) = \sum_{i=1}^{n} \theta_i F_i G_i(t) \tag{1}$$

with $$F_i = \delta \sqrt{\frac{\sigma_i}{\mu_i}} \tag{2}$$

and $$G_i(t) = \frac{t^\gamma}{1 + \alpha\left(\beta\frac{t}{\tau_i}\right)^m e^{\beta\frac{t}{\tau_i}}} \tag{3}$$

where α, β, γ, δ and m are dependent on the geometry of the material, $\sigma_i$ represents the conductivity of an area i of the material and $\mu_i$ represents the magnetic permeability of the area i of the material, and the areas i (i=1, 2, . . . , n) together generate the signal V(t). Here α, β, γ, δ and m are also dependent on the geometry of the transmitting antenna and receiving antenna, as well as on the relative positions of the material, the transmitting and the receiving antenna.

If the above-mentioned method for describing the electromagnetic signal generated by the eddy currents is used, the following method for determining properties of the object can be carried out.

Using a predetermined algorithm, parameters $\tau_i$ and/or $$\frac{\sigma_i}{\mu_i}$$

or parameters to be derived from these parameters of the equation $$V(t) = \sum_{i=1}^{n} \theta_i F_i G_i(t) \quad (1)$$

or an equation to be derived therefrom, with $$F_i = \delta \sqrt{\frac{\sigma_i}{\mu_i}} \quad (2)$$

$$G_i(t) = \frac{t^\gamma}{1 + \alpha\left(\beta\frac{t}{\tau_i}\right)^m e^{\beta\frac{t}{\tau_i}}} \quad (3)$$

$$i = 1, 2, \ldots n \quad (4)$$

and $$\sum_{i=1}^{n} \theta_i = 1 \quad (5)$$

are selected such that V(t), according to a predetermined criterion of the algorithm, corresponds to the course over time of the detected electromagnetic signal.

Suppose, for instance, that the thickness d of the measuring area 22 of the measuring object 16 is to be determined. The assumption is that the thickness d is uniform, that is, $d_1 = d_2 = d$. Because the geometry of the measuring object 16, the transmitting antenna 2, the receiving antenna 6 and their relative positions in this example are known, $\alpha$, $\beta$, $\gamma$, $\delta$ and m can be calculated in a manner known per se, using a simulation model. These parameters can therefore be assumed to be known. It is also assumed that the material of the measuring object is homogeneous. In other words, the magnetic permeability and the electrical conductivity are the same in the entire measuring area 22. This means that in itself no distinction needs to be made between signals coming from the area i=1 on the one hand and the area i=2 on the other. In the above-mentioned formula 1, therefore, i=n=1 can be selected. The magnetic permeability $\mu_1$ of the material will hereinafter be designated $\mu_0$, while the conductivity $\sigma_1$ of the material will hereinafter be designated $\sigma_0$.

First of all, $\mu_0$ or $\sigma_0$ is to be determined on the basis of a calibration measurement. This calibration measurement is carried out as follows.

Figure 2:
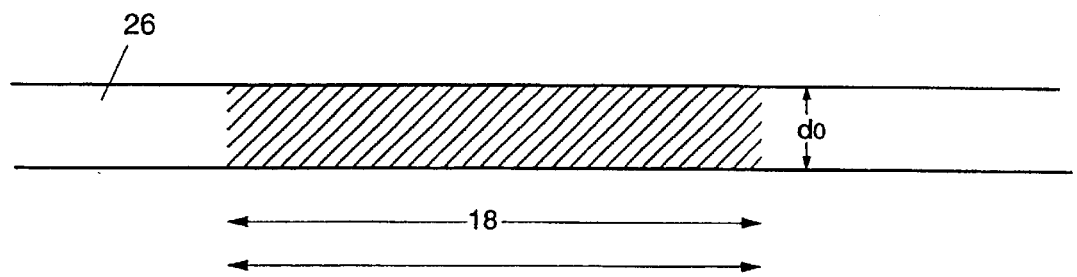
FIG. 2 shows a possible embodiment of a test object.

The measuring object 16 is replaced by a test object 26 (see FIG. 2) whose thickness do is known. Then the apparatus 1 is activated. It measures the signal G(t) coming from the test object 26. The computer 10 then selects, according to a predetermined algorithm, the parameters $\mu_0$ and $\sigma_0$ such that according to a predetermined criterion of the algorithm, V(t) corresponds to the course over time of the electromagnetic signal S(t) generated by the eddy currents in the test object and detected by the receiving antenna 4. Further, according to the invention, $\tau_i = \mu_i \sigma_i d_i^2$ (6). Because i=n=1, it follows from formula 6 that $\tau_1 = \mu_0 \sigma_0 d_0^2$. By substituting $\tau_1$ in formula 1 by $\mu_0 \sigma_0 d_0^2$, it is possible, for instance according to the Levenberg-Marquardt algorithm, to determine $\mu_0$ and $\sigma_0$ such that V(t) corresponds accurately to S(t). Thus, $\mu_0$ and $\sigma_0$ have been determined.

The test object 26 is then replaced by the measuring object 16. Again, using the transmitting antenna 2, a changing electromagnetic field is generated. Again, the electromagnetic signal S(t) subsequently detected by the receiver unit 8 is applied to the computer 10. Then the parameters $\tau_1$ and $$\frac{\sigma_1}{\mu_1}$$

(or parameters which can be derived therefrom) of the equation $$V(t) = \sum_{i=1}^{n} \theta_i F_i G_i(t) \quad (1)$$

or an equation derivable therefrom, with $$F_i = \delta \sqrt{\frac{\sigma_i}{\mu_i}} \quad (2)$$

$$G_i(t) = \frac{t^\gamma}{1 + \alpha\left(\beta\frac{t}{\tau_i}\right)^m e^{\beta\frac{t}{\tau_i}}} \quad (3)$$

$$i = n = 1 \quad (4)$$

and $$\theta_1 = 1 \quad (5)$$

are selected such that V(t), according to a predetermined criterion of the algorithm, corresponds to the course over time of the detected electromagnetic signal S(t).

Thus, $\tau_1$ and $$\frac{\sigma_1}{\mu_1}$$

of the measuring object have been determined. Further, according to formula 6, $\tau_1 \sigma_1 d_1^2$. This means that $d_1$ can be determined on the basis of the $\tau_1$ and $$\frac{\sigma_1}{\mu_1}$$

found, and on the basis of the known value $\mu_1 = \mu_0$ or $\sigma_1 = \sigma_0$. The thus obtained value of $d_1$ corresponds to the homogeneous thickness $d_0$ of the material.

It may also happen, however, that the material of the measuring object 16 includes a defect or flaw. In that case, the thickness of the measuring object is not the same throughout. In the example of FIG. 1, the assumption was that the thickness in the areas i=1 equals $d_1$, while the thickness in the area i=2 equals $d_2$. The values for $d_1$ and $d_2$ can presently be determined as follows.

In formula 1, n is selected to be greater than or equal to 2. In this example, n is selected to be, for instance, 4. Again, the assumption is that the magnetic and electrical properties of the material are homogeneous. In other words, $\mu_1 = \mu_2 = \mu_3 = \mu_4 = \mu_0$ and $\sigma_1 \sigma_2 = \sigma_3 = \sigma_4 = \sigma_0$. $\mu_0$ and $\sigma_0$, as has been discussed above, can again be determined using a test object.

Then, using the predetermined algorithm, the parameters $\tau_i$ and $$\frac{\sigma_i}{\mu_i}$$

(or parameters that can be derived therefrom) of the equation $$V(t) = \sum_{i=1}^{n=4} \theta_i F_i G_i(t) \qquad (1)$$

or an equation to be derived therefrom, with $$F_i = \delta \sqrt{\frac{\sigma_i}{\mu_i}} \qquad (2)$$

$$G_i(t) = \frac{t^\gamma}{1 + \alpha\left(\beta\frac{t}{\tau_i}\right)^m e^{\beta\frac{t}{\tau_i}}} \qquad (3)$$

$$i = 1, 2, \ldots n = 4 \qquad (4)$$

and $$\sum_{i=1}^{n=4} \theta_i = 1 \qquad (5)$$

are selected such that V(t), according to a predetermined criterion of the algorithm, corresponds to the course over time of the detected electromagnetic signal S(t).

Again, for fitting the parameters of the model, use is made of the Levenberg-Marquardt algorithm. If the material is indeed homogeneous, it will appear that the determined ratio of $\mu_i$ and $\sigma_i$ corresponds for each i to the ratio of $\mu_0$ and $\sigma_0$. Obviously, it is also possible in formula 1 for each i to directly replace the ratio of $\mu_i$ and $\sigma_i$ by the known ratio of $\mu_0$ and $\mu_0$. In that case, using the algorithm, only the parameter $\tau_i$ for i=1-4 and $\theta_i$ for i=1-4 is determined. Physically, of the measuring area 22, the fraction $\theta_1 F_1 G_1(t)$ can be regarded as the signal generated by the area i=1, while the signal $\theta_2 F_2 G_2(t)$ comes from the area i=2. Further, in this example, the algorithm will yield that the parameters $\theta_3$ and $\theta_4$ are substantially equal to 0, because only two different thicknesses occur in the measuring area 22. The signal $\theta_1 F_1 G_1(t)$ can then be taken as the signal coming from the relatively large area i=1 of the thickness $d_1$, while the signal $\theta_2 F_2 G_2(t)$ comes from the relatively small area i=2 of a lesser thickness $d_2$. The area i=2 of the lesser thickness then includes a so-called defect.

Then, on the basis of the values of $\tau_1$ and $\tau_2$, the thickness $d_1$ and the thickness $d_2$ are determined, using the formula $\tau_i = \mu_i \sigma_i d_i^2$. Here, it can again be stated that $\mu_i = \mu_0$ and $\sigma_i = \sigma_0$.

Using the apparatus according to FIG. 1, it is also possible to determine the permeability $\mu_0$ and the conductivity $\sigma_0$ of a homogeneous material. Such a determination corresponds to the above-discussed calibration.

When the material is inhomogeneous, either spread in the conductivity or spread in the relative permeability of the material, given a known wall thickness, can be determined. This can be done as follows.

Suppose that the material of FIG. 1 satisfies $d_1 = d_2 = d_0$. Further, the permeability $\mu_1$ of the area i=1 is equal to the permeability $\mu_2$ of the area i=2. In other words, the permeability equals $\mu_0$. On the basis of the formula $\tau_i = \mu_i \sigma_i d_i^2$, $\tau_i$ can be expressed in $\sigma_i$. Thus, $\tau_i = \mu_0 \sigma_i d_0^2$. This value of $\tau_i$ can presently be substituted in formula 1. Formula 1 presently contains the variables $\theta_i$ and $\sigma_i$. In accordance with the invention, these variables can be fitted to the measured signal S(t).

Fitting is carried out, for instance, for n=3. Thus, values are found for $\theta_1$, $\theta_2$ and $\theta_3$, and for $\sigma_1$, $\sigma_2$ and $\sigma_3$. Here, $\theta_3$ will be substantially equal to 0, since in the measuring object in this example, in good approximation, two different conductivities occur, viz. $\sigma_1$ for the area i=1 and $\sigma_2$ for the area i=2. The values found for $\sigma_1$ and $\sigma_2$ represent a spread in the conductivity in the material. Entirely analogously, a spread in the permeability can be calculated if the wall thickness is equal to $d_0$ throughout, and the conductivity is equal to $\sigma_0$ throughout. Such variants are all understood to fall within the scope of the invention.

In carrying out the above-mentioned measurements, the assumption is that the parameters depending on the geometry do not change. It is also possible, however, to assume that the parameters change in a known manner. In that case, in the measurement, the signal strength is determined. On the basis thereof, the lift-off can be calculated. The lift-off is the distance between, on the one hand, the receiving and transmitting antennas arranged in mutual proximity and, on the other, the surface of the measuring object. Then, on the basis of the lift-off, the correct model parameters ($\alpha$, $\beta$, $\gamma$, $\delta$ and m) can be calculated, given a known geometry. This calculation can then be a function of the distance mentioned. If the geometry of the object and/or the transmitting and receiving antennas is not known, the model parameters $\alpha$, $\beta$, $\gamma$, $\delta$ and m cannot be calculated. It is possible, however, as discussed above, using a test object, to determine the model parameters $\alpha$, $\beta$, $\gamma$, $\delta$ and m for a number of mutually different distances. On the basis of the different values that are found for the model parameters for different distances, it is possible to determine in a manner known per se a model in which the model parameters are a linear function of the distance mentioned.

Such variants are all understood to fall within the scope of the invention.

What is claimed is:

1. A method for determining properties of an electrically conductive object to be measured, comprising the steps of:

transmitting a time varying electromagnetic field from a transmit antenna to said object for generating eddy currents in said object;

detecting an electromagnetic signal S(t) generated by said eddy currents using a receiving antenna; and determining properties of said object from said signal S(t) by selecting certain $\tau_i$ and $$\frac{\sigma_i}{\mu_i}$$

such that $$S(t) = \sum_{i=1}^{n} \theta_i F_i G_i(t) \qquad (1)$$

with $$F_i = \delta \sqrt{\frac{\sigma_i}{\mu_i}} \qquad (2)$$

-continued $$G_i(t) = \frac{t^\gamma}{1 + \alpha\left(\beta\frac{t}{\tau_i}\right)^m e^{\beta\frac{t}{\tau_i}}} \quad (3)$$

$$i=1, 2, \ldots n \quad (4)$$

and $$\sum_{i=1}^{n} \theta_i = 1 \quad (5)$$

wherein $\alpha$, $\beta$, $\gamma$, $\delta$, and m are real numbers dependent on geometry of said object, of said transmitting antenna and of said receiving antenna;

wherein said real numbers are further dependent on relative positions of said object, said transmitting antenna and said receiving antenna;

wherein $\mu_i$ represents magnetic permeability of an area i of said object and $\sigma_i$ represents electrical conductivity of an area i of said object; and wherein said areas i (i=1, 2, ... n) together generate said electromagnetic S(t).

2. The method in accordance with claim 1 and further comprising the step of selecting i=n=1 and wherein $\mu_i=\mu_0$ and is a known value, and wherein said thickness $d_i$ of an area i of said object is determined from equation $\tau_i=\mu_i\sigma_i d_i^2$.

3. The method in accordance with claim 1 and further comprising the steps of selecting i=n=1 and wherein $\sigma_1=\sigma_0$ is a known value and wherein said thickness $d_i$ of an area i of said object is determined from equation $\tau_i=\mu_i\sigma_i d_i^2$.

4. The method in accordance with claim 1 wherein n≧2, wherein $\mu_i$ has a known value and wherein the thickness $d_i$ of areas i of said object are determined from equation $\tau_i=\mu_i\sigma_i d_i^2$.

5. The method in accordance with claim 1 wherein n≧2, wherein $\sigma_i$ has a known value and wherein the thickness $d_i$ of areas i of said object are determined from equation $\tau_i=\mu_i\sigma_i d_i^2$.

6. The method in accordance with claim 4 wherein said object to be measured has a known homogeneous electrical conductivity $\sigma_0$ and a known homogeneous magnetic permeability $\mu_0$ and wherein for every value of i, $\mu_1=\mu_0$ and $\sigma_1=\sigma_0$.

7. The method in accordance with claim 2 wherein said object to be measured is formed of a pre-defined material and wherein said method further comprises the step of generating eddy currents in a test object constructed of said pre-defined material and having a thickness $d_i=d_0$(i=1, 2, ..., n) and the step of selecting parameters $\mu_0$ and $\sigma_0$ such that V(t) corresponds to a course, over time, of an electromagnetic signal generated by said eddy currents in said test object as detected by said receiving antenna.

8. The method in accordance with claim 6 wherein said object to be measured is formed of a pre-defined material and wherein said method further comprises the step of generating eddy currents in a test object constructed of said pre-defined material and having a thickness $d_i=d_0$(i=1, 2, ..., n) and the step of selecting parameters $\mu_0$ and $\sigma_0$ such that V(t) corresponds to said course, over time, of an electromagnetic signal generated by said eddy currents in said test object as detected by said receiving antenna.

9. The method in accordance with claim 1 wherein i=n=1 and said thickness d of said object to be measured is known over an area to be measured, wherein values $\mu_i$ and $\sigma_i$ are determined from equation $\sigma_i=\mu_i\sigma_i d_0^2$.

10. The method in accordance with claim 1 wherein n>1 and wherein said thickness of $d_0$ of said object to be measured is known and is constant over an area to measured and for each value of i, $d_i=d_0$ and wherein $\mu_i$ is determined from $\tau_i=\mu_i\sigma_i d_0^2$.

11. The method in accordance with claim 1 wherein n>1 and wherein said thickness of $d_0$ of said object to be measured is known and is constant over an area to be measured and for each value of i, $d_i=d_0$ and wherein $\sigma_i$ is determined from $\tau_i=\mu_i\sigma_i d_0^2$.

12. The method in accordance with claim 1 wherein $\alpha$, $\beta$, $\gamma$, $\delta$, and m are determined from a predetermined simulation model wherein said object, said transmit antenna, and said receive antenna each have a predefined geometry and are disposed in predetermined relative positions.

13. The method in accordance with claim 1 wherein parameters $\alpha$, $\beta$, $\gamma$, $\delta$, and m in a test object having known parameters $\mu_i$, $\sigma_i$, $d_i$ and further comprising the steps of:

transmitting a time varying electromagnetic field to said object from a transient antenna for generating eddy currents in said object;

detecting signals generated by said eddy currents in a receiving antenna;

selecting parameters $\alpha$, $\beta$, $\gamma$, $\delta$ according to a predetermined algorithm such that V(t) for known values of parameters $\tau_i$ and $$\frac{\sigma_i}{\mu_i}$$

correspond to a course overtime of electromagnetic signals received from said test object.

14. Apparatus for determining properties of an object to be measured, said apparatus comprising:

a transmitter unit;

a transmit antenna coupled to said transmitter unit;

a receiver unit;

a receiver antenna coupled to said receiver unit; and a computer coupled to said transmitter unit and said receiver unit;

said computer operative to control said transmitter to transmit a time varying electromagnetic field to said object for generating eddy current in said object;

said receiver unit operative to detect an electromagnetic signal S(t) for determining parameters $\tau_i$ and $$\frac{\sigma_i}{\mu_i}$$

such that:

$$S(t) = \sum_{i=1}^{n} \theta_i F_i G_i(t) \quad (1)$$

with $$F_i = \delta\sqrt{\frac{\sigma_i}{\mu_i}} \quad (2)$$

$$G_i(t) = \frac{t^\gamma}{1 + \alpha\left(\beta\frac{t}{\tau_i}\right)^m e^{\beta\frac{t}{\tau_i}}} \quad (3)$$

$$i=1, 2, \ldots n \quad (4)$$

and $$\sum_{i=1}^{n} \theta_i = 1 \quad (5)$$

wherein $\alpha$, $\beta$, $\gamma$, $\delta$ are real number representing characteristics of geometry of said object, said transmitting antenna and said receiving antenna and of relative positions of said object, said transmitting antenna and said receiving antenna and wherein $\mu_i$ represents magnetic permeability of an area i of said object and $\sigma_i$ represents electrical conductivity of said area i of said object; and wherein said areas i(i=1,2), . . . n) together generate said electromagnetic signal S(t).

* * * * *